United States Patent [19]

Andrews et al.

[11] Patent Number: 4,565,888

[45] Date of Patent: Jan. 21, 1986

[54] SUBSTITUTED SALICYLIC ACID AMIDE ANTHELMINTICS

[75] Inventors: Peter Andrews, Wuppertal; Horst Böshagen; Heinrich Kölling, both of Haan, all of Fed. Rep. of Germany

[73] Assignee: Bayer Aktiengesellschaft, Leverkusen, Fed. Rep. of Germany

[21] Appl. No.: 691,032

[22] Filed: Jan. 11, 1985

[30] Foreign Application Priority Data

Jan. 20, 1984 [DE] Fed. Rep. of Germany ....... 3401950

[51] Int. Cl.$^4$ ............................................. C07C 103/76
[52] U.S. Cl. ..................................... 564/179; 560/138; 514/546; 514/617
[58] Field of Search ................ 564/179; 514/617, 546; 560/138

[56] References Cited

U.S. PATENT DOCUMENTS

| | | | |
|---|---|---|---|
| 3,715,395 | 2/1973 | Mrozik et al. | 564/179 |
| 3,719,707 | 3/1973 | Mrozik | 560/138 |
| 3,798,258 | 5/1974 | Patchett et al. | 564/179 |
| 3,914,418 | 10/1975 | Patchett et al. | 564/179 |
| 3,966,964 | 6/1976 | Kurz et al. | 514/546 |

FOREIGN PATENT DOCUMENTS 0119446 9/1984 European Pat. Off. .
2610837 9/1976 Fed. Rep. of Germany .

*Primary Examiner*—Charles F. Warren
*Assistant Examiner*—R. A. Picard
*Attorney, Agent, or Firm*—Sprung, Horn, Kramer & Woods

[57] ABSTRACT

Anthelmintically active novel substituted salicylic acid amides of the formula

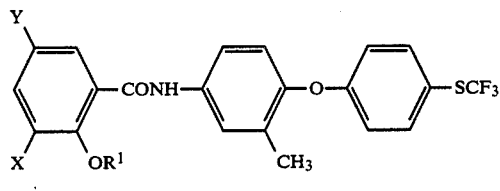

in which
X and Y each independently is halogen, and,
$R^1$ is hydrogen or acetyl.

5 Claims, No Drawings

SUBSTITUTED SALICYLIC ACID AMIDE ANTHELMINTICS

The present invention relates to new substituted salicylic acid amides, processes for their preparation and their use as medicaments, in particular as anthelmintics.

It is already known that substituted salicylic acid amides have an anthelmintic action (in this context, see, inter alia, DOS (German Published Specification) No. 2,610,837 and U.S. Pat. No. 3,914,418).

The new substituted salicylic acid amides of the formula (I)

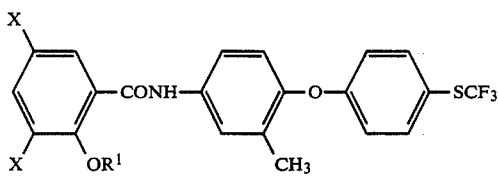

in which
X and Y represent identical or different halogens and, $R^1$ represents hydrogen or the acetyl radical, have been found.

It has furthermore been found that the new salicylic acid amides of the formula (I)

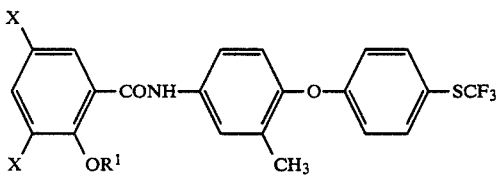

in which
X and Y represent identical or different halogens and, $R^1$ represents hydrogen or the acetyl radical, are obtained when the chlorides of the salicylic acids or their acetyl derivatives of the formula (II)

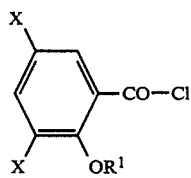

in which
$R_1$, X and Y have the abovementioned meaning, are reacted with the amine of the formula (III)

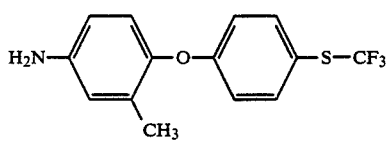

in the presence of a diluent, if appropriate in the presence of an acid-binding agent, and, if appropriate, the acyl radical is split off.

Surprisingly, the salicylic acid amides according to the invention are distinguished by a broader action spectrum, with a good anthelmintic action, in comparison with other anthelmintics. They exhibit a good compatibility and a synergistic action in combination with other anthelmintic compounds. Moreover, they break the benzimidazole-resistance of known anthelmintics.

Compounds of the formula (I) in which X and Y represent chlorine, bromine or iodine, in particular iodine, and $R^1$ represents hydrogen are preferred.

If 3,5-diiodosalicylyl chloride is used as the starting material of the formula (II), the reaction with the amine of the formula (III) can be represented by the following equation:

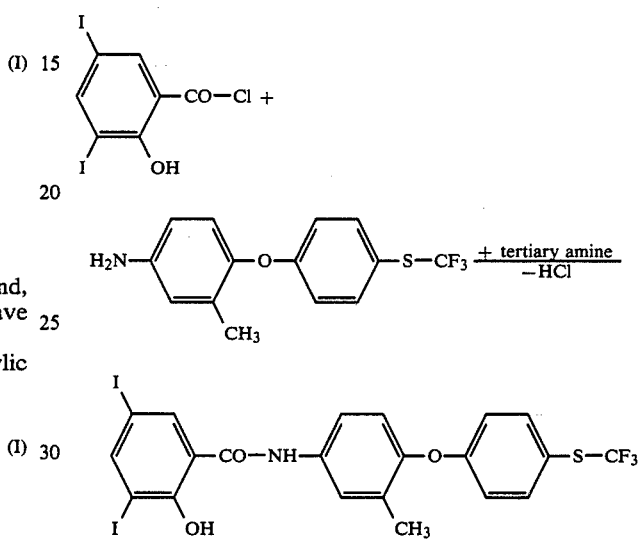

If 3,5-diiodo-acetylsalicylyl chloride is used as the starting material, the course of the reaction can be formulated as follows:

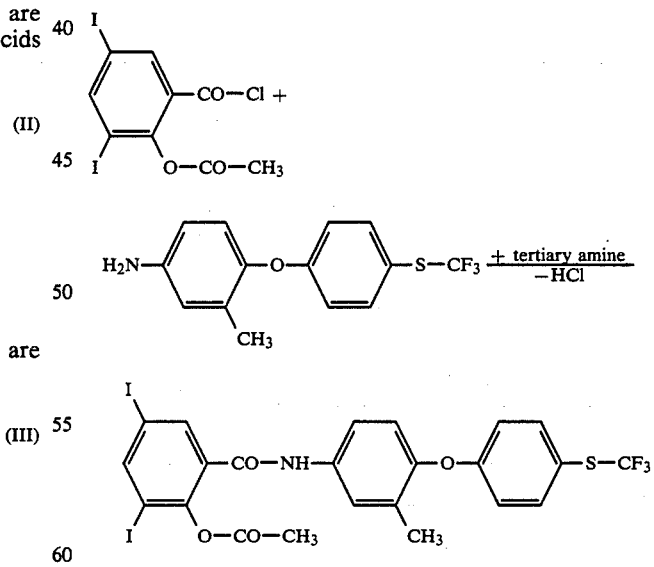

The acetyl group can then be hydrolyzed by methods which are known from the literature. The substituted salicylic acid chlorides of the formula (II) used as starting substances are known, or they can be prepared by methods analogous to those known from the literature. The compound of the formula (III) is known (DE-OS (German Published Specification) 2,413,722).

Possible diluents in carrying out the process according to the invention are inert organic solvents, in particular ethers, such as dioxane or tetrahydrofuran.

Possible acid-binding agents are inorganic bases, such as NaOH, KOH, $Na_2CO_3$ or $NaHCO_3$, or organic bases such as diethylamine or triethylamine.

The reaction temperatures can be varied within a substantial range. In general, the reaction is carried out between 50° and 120° C. The reaction is carried out under normal pressure.

The hydrolysis is carried out with acids or bases at temperatures between 50° and 100° C., preferably in aqueous or water-containing diluents, in particular alcohols, such as methanol or ethanol. Acids which may be mentioned are mineral acids, such as hydrochloric acid and sulphuric acid. Bases which may be mentioned are alkali metal hydroxides, such as sodium or potassium hydroxide.

The new compounds have a broad action against endoparasites which are pathogenic to humans and animals. Above all, they have an action against trematodes and nematodes, in particular liver fluke and stomach and intestinal nematodes in ruminants. Moreover, they also have an action against those stomach and intestinal nematodes which are resistant towards the usual benzimidazole anthelmintics and thus can no longer be adequately treated.

The action has been tested in animal experiments following oral, parenteral and dermal administration to experimental animals highly infected with parasites. The dosages used were tolerated very well by the experimental animals.

The new active compounds can be used as anthelmintics both in human medicine and in veterinary medicine.

The new active compounds can be converted into the customary formulations in a known manner.

The new compounds can be administered together with other customary anthelmintics.

The new compounds can be used either as such or in combination with pharmaceutically acceptable excipients. Possible forms of administration in combination with various inert excipients are tablets, capsules, granules, aqueous suspensions, injectable solutions, emulsions and suspensions, elixirs, syrup, pastes and the like. Excipients of this type include solid diluents or fillers, a sterile, aqueous medium and various non-toxic organic solvents and the like. The tablets and the like envisaged for oral administration can, of course, be provided with added sweetener and the like. In the abovementioned case, the therapeutically active compound should be present in a concentration of about 0.5 to 90% by weight of the total mixture, that is to say in amounts which suffice to achieve the abovementioned dosage range.

The formulations are prepared in a known manner, for example by extending the active compounds with solvent and/or excipients, if appropriate with the use of emulsifying agents and/or dispersing agents, and, for example when using water as the diluent, organic solvents can be used, if appropriate, as auxiliary solvents.

Examples of auxiliary substances which may be mentioned are: water, non-toxic organic solvents, such as paraffins (for example, petroleum fractions), vegetable oils (for example groundnut-(sesame oil), alcohols (for example ethyl alcohol and glycerol), glycols (for example propylene glycol and polyethylene glycol) and water; solid excipients, such as, for example, natural rock powders (for example kaolins, aluminas, talc and chalk), synthetic rock powders (for example highly dispersed silica and silicates) and sugars (for example raw sugar, lactose and glucose); emulsifying agents, such as nonionic and anionic emulsifiers (for example polyoxyethylene fatty acid esters, polyoxyethylene fatty alcohol ethers, alkylsulphonates and arylsulphonates), dispersing agents (for example methylcellulose, starch and polyvinylpyrrolidone) and lubricants (for example magnesium stearate, talc, stearic acid and sodium lauryl-sulphate.

In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets.

In the case of aqueous suspensions and/or elixirs which are intended for oral use, the active compound can be mixed with various flavor-improving agents or colorants, in addition to the abovementioned auxiliary substances.

In the case of parenteral use, solutions of the active compounds can be employed, using suitable liquid excipients.

The active compounds can also be contained in capsules, tablets, pastilles, dragees, ampoules and the like in the form of dosage units, each dosage unit being adjusted so that it yields a single dose of the active constituent.

The new compounds can also be present in the formulations in mixtures with other known active compounds used for treating infections and/or diseases in veterinary medicine/human medicine, in particular L-2,3,5,6-tetrahydro-6-phenyl-imidazo-thiazole, benzimidazole carbamates, praziquantel and febantel.

The new active compounds can be used in the customary manner. Administration is preferably effected orally, but parenteral, in particular subcutaneous, and also dermal administration are also possible.

In general, it has proved advantageous to administer the new active compounds in amounts of about 1 to about 100 mg per kg of body weight daily to achieve effective results.

Nevertheless, it can at times be necessary to deviate from the amounts mentioned, and in particular to do so as a function of the body weight of the experimental animal and of the nature of the administration method, but also because of the species of animal and its individual behaviour towards the medicament, and the nature of the formulation of the medicament and the time or interval at which administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine and in veterinary medicine. The general sense of the above statements also applies.

EXAMPLE 1

40.8 g (0.1 mol) of 3,5-diiodosalicylyl chloride of melting point 94° C.—dissolved in tetrahydrofuran—are added dropwise to a solution of 26.7 g (0.1 mol) of 3-methyl-4-(4-trifluoromethylthiophenoxy)-aniline (oily) and 10.1 g (0.1 mol) of triethylamine in 300 cm³ of tetrahydrofuran at room temperature, with stirring. Stirring is then continued at 60° C. for a period of 3 hours and, after cooling, the mixture is filtered, the solvent is stripped off in vacuo, the oily residue is extracted by stirring with water, the water is decanted off and the residue is recrystallized from ligroin—melting point of the 3,5-diiodo-3'-methyl-4'-(4-trifluoromethylthiophenoxy)-salicylic acid anilide: 144° C.

EXAMPLE 2

45 g (0.1 mol) of 3,5-diiodoacetylsalicylyl chloride of melting point 98° C.—dissolved in tetrahydrofuran—are added dropwise to a solution of 26.7 g (0.1 mol) of 3-methyl-4-(4-trifluoromethylthiophenoxy)-aniline (oily) and 10.1 g of triethylamine in 300 cm³ of tetrahydrofuran at room temperature, with stirring. Stirring is then continued at 60° C. for 3 hours and, after cooling, the mixture is filtered, the solvent is evaporated off in a rotary evaporator in vacuo, the oily residue is extracted with water and the water is decanted off. The 2-acetoxy-3,5-diiodo-3'-methyl-4'-(4-trifluoromethylthiophenoxy)-benzanilide crystallizes under a little methanol (melting point 163° C.).

10 g of this compound are stirred in 100 ml of 0.5N NaOH at 60° C. for 1 hour. The compound of Example 1 is then isolated.

The following compounds are obtained analogously to Example 1 and 2:

| Example No. | R₁ | X | Y | Melting point (°C.) |
| --- | --- | --- | --- | --- |
| 3 | H | Cl | Cl | 98 |
| 4 | H | Br | Br | 115 |
| 5 | H | Br | Cl | 110 |
| 6 | COCH₃ | I | I | 163 |
| 7 | COCH₃ | Cl | Cl | 135 |
| 8 | COCH₃ | Br | Br | 141 |
| 9 | COCH₃ | Br | Cl | 138 |

EXAMPLE A

Rats infected experimentally with metacercaria of *Fasciola hepatica* were treated orally by means of a stomach tube after the infection.

(a) One group of animals was treated once on each of three successive days after the infection. The animals were sacrificed two weeks after the infection and the number of juvenile liver fluke in the liver parenchyma were determined.

(b) One group of animals was treated once after the infection. The animals were sacrificed 12 weeks after the infection and the number of adult liver fluke were determined.

The following table shows the minimum dose required to achieve at least 95% parasite reduction in comparison with an untreated control:

| | Minimum dose for treatment | |
| --- | --- | --- |
| | (a) | (b) |
| 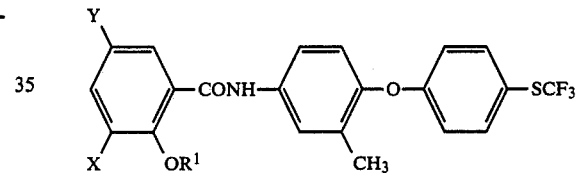 (known) | 3 × 100 mg | 25 mg |
| 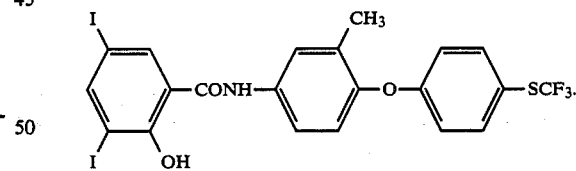 (known) | 3 × 100 mg | 500 mg |
| according to the invention 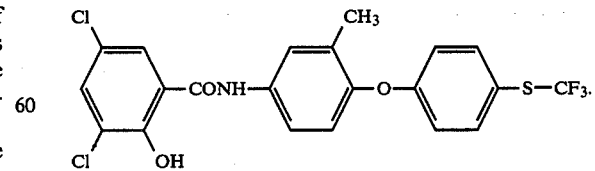 | 3 × 25 mg | 10 mg |

It will be appreciated that the instant specification and examples are set forth by way of illustration and not limitation, and that various modifications and changes may be made without departing from the spirit and scope of the present invention.

We claim:

1. A substituted salicylic acid amide of the formula

![structure]

in which
X and Y each independently is halogen, and,
R¹ is hydrogen or acetyl.

2. A compound according to claim 1, wherein such compound is 3,5-diiodo-3'-methyl-4'-(4-trifluoromethylthiophenoxy)-salicylic acid anilide of the formula ![structure]

3. A compound according to claim 1 wherein such compound is 3,5-dichloro-3'-methyl-4'-(4-trifluoromethylthiophenoxy)-salicylic acid aniline of the formula ![structure]

4. An anthelmintic composition comprising an anthelmintic effective amount of a compound according to claim 1 in admixture with a diluent.

5. A unit dose of a composition according to claim 3 in the form of a tablet, capsule or ampule.

* * * * *